(12) United States Patent
Lin

(10) Patent No.: US 9,126,027 B2
(45) Date of Patent: Sep. 8, 2015

(54) EYEBROW TATTOO MACHINE CAPABLE OF ACTIVATING BOTH SWINGING MOVEMENT AND UP-AND-DOWN MOVEMENT

(71) Applicant: MEI-CHI-NA HSINYEN CO., LTD., Taipei (TW)

(72) Inventor: Su-Lin Lin, Taipei (TW)

(73) Assignee: MEI-CHI-NA-HSINYEN CO., LTD., Taipei (TW)

( * ) Notice: Subject to any disclaimer, the term of this patent is extended or adjusted under 35 U.S.C. 154(b) by 310 days.

(21) Appl. No.: 13/905,238

(22) Filed: May 30, 2013

(65) Prior Publication Data
US 2014/0358173 A1    Dec. 4, 2014

(51) Int. Cl.
*A61B 17/34* (2006.01)
*A61M 37/00* (2006.01)
*B43K 5/00* (2006.01)

(52) U.S. Cl.
CPC .................................. *A61M 37/0076* (2013.01)

(58) Field of Classification Search
CPC ..................... A61M 37/0076; A61M 37/0092; A01K 11/005
USPC .................................... 81/9.22; 606/185, 186
See application file for complete search history.

(56) References Cited

U.S. PATENT DOCUMENTS

| | | | | |
|---|---|---|---|---|
| 4,031,783 A | * | 6/1977 | Paul et al. ....................... | 81/9.22 |
| 4,204,438 A | * | 5/1980 | Binaris et al. ................... | 81/9.22 |
| 4,796,624 A | * | 1/1989 | Trott et al. ...................... | 606/185 |
| 4,914,988 A | * | 4/1990 | Chang ............................. | 81/9.22 |
| 5,472,449 A | * | 12/1995 | Chou .............................. | 606/186 |
| 5,741,290 A | * | 4/1998 | Hsieh ............................. | 606/186 |
| 6,033,421 A | * | 3/2000 | Theiss et al. ................... | 606/186 |
| 2003/0195542 A1 | * | 10/2003 | Lee ................................ | 606/186 |
| 2004/0116953 A1 | * | 6/2004 | Dixon ............................ | 606/186 |
| 2004/0143275 A1 | * | 7/2004 | Chen .............................. | 606/133 |
| 2005/0010236 A1 | * | 1/2005 | Frister ............................ | 606/116 |
| 2007/0060937 A1 | * | 3/2007 | Liu ................................. | 606/185 |
| 2008/0306502 A1 | * | 12/2008 | Lisec et al. .................... | 606/186 |
| 2010/0191268 A1 | * | 7/2010 | Lee ................................ | 606/185 |
| 2011/0048174 A1 | * | 3/2011 | Lin ................................. | 81/9.22 |
| 2012/0123462 A1 | * | 5/2012 | Lee ................................ | 606/185 |
| 2012/0279330 A1 | * | 11/2012 | Lin ................................. | 74/45 |

* cited by examiner

*Primary Examiner* — Julian W Woo
*Assistant Examiner* — Christopher L Templeton
(74) *Attorney, Agent, or Firm* — Bacon & Thomas, PLLC

(57) ABSTRACT

The present invention is to provide an eyebrow tattoo machine, which includes a housing; a swinging movement-activating motor located inside the housing and having one end provided with a transmission shaft; an eccentric sleeve mounted around the transmission shaft and protrudingly provided with an eccentric lever offset from the center thereof and facing away from the motor; and a tattoo needle actuation mechanism positioned and pressed against by screws in the housing and configured for driving a tattoo needle at one end thereof to move upward-and-downward along an axis of the machine, and having the other end provided with a round-ended slot. The eccentric lever extends into the round-ended slot so that, once the motor is turned on, the eccentric lever can drive the entire tattoo needle actuation mechanism to swing from side to side with respect to the axis of the machine by using the screws as the fulcrum.

6 Claims, 4 Drawing Sheets

EYEBROW TATTOO MACHINE CAPABLE OF ACTIVATING BOTH SWINGING MOVEMENT AND UP-AND-DOWN MOVEMENT

FIELD OF THE INVENTION

The present invention relates to an eyebrow tattoo machine, more particularly to an eyebrow tattoo machine having a tattoo needle actuation mechanism which is positioned and pressed against by screws in a housing thereof, configured for driving a tattoo needle into up-and-down displacement along an axis of the eyebrow tattoo machine, and capable of being driven to swing from side to side with respect to the axis of the eyebrow tattoo machine by using the screws as the fulcrum.

BACKGROUND OF THE INVENTION

To women in the modern society, eyebrow tattooing means more than saving the time required for daily makeup application. Eyebrows can define a person's countenance—be it a happy, angry, or sad one—or even represent either gender. Given today's cosmetic surgery techniques, eyebrows are the only facial feature that can be reshaped without causing much physical pain. If eyes are a window to the soul, then eyebrows, which allow modification to the greatest extent as compared with the other facial features, can be said to be the light above that window, for a pair of nicely shaped eyebrows can definitely accentuate the beauty of the eyes. This is the main reason why eyebrow tattooing has become increasingly popular.

Traditionally, eyebrow tattooing was carried out solely by hand, and if the pigment was not implanted to a uniform depth, the resultant eyebrow tattoos might look asymmetric or have other defects. To overcome the various drawbacks of the traditional manual eyebrow tattooing method, mechanical eyebrow tattoo machines were developed to make more natural-looking eyebrow tattoos.

Generally speaking, a conventional eyebrow tattoo machine consists of a transmission mechanism and a needle mounting mechanism, wherein the transmission mechanism is configured for driving the tattoo needle in the needle mounting mechanism into reciprocal up-and-down movement along the central axis of the eyebrow tattoo machine. In use, an eyebrow tattooist coats the tip of the tattoo needle with ink and, by means of the tattoo needle, tattoos predetermined patterns on a person's face according to the person's desired eyebrow shapes. As a conventional eyebrow tattoo machine typically uses a single tattoo needle, the tattooing area of each stab is quite small. The eyebrow tattoo machine, once turned on, must be supported with the eyebrow tattooist's wrist, held steadily above the skin of the person being tattooed, and continuously maneuvered with the tattooist's hand in order to create a dense look of eyebrow hair.

The operation described above is physically demanding. In particular, the tattooist's wrist is intensely and repeatedly, if not excessively, used during operation, and such heavy workload may cause occupational injury to the wrist. A common injury resulting from the aforesaid occupational activity is the carpal tunnel syndrome, which is common among those who are required to use their wrists repeatedly, such as mechanics, carpenters, and typists. The carpal tunnel syndrome is typically found in a person's dominant hand and will aggravate with workload. According to the foregoing description, the working condition of an eyebrow tattooist is very likely to cause the carpal tunnel syndrome.

The issue to be addressed by the present invention is to design an eyebrow tattoo machine capable of solving the aforementioned problems. It is highly desirable that an eyebrow tattoo machine can be operated with less effort than traditionally required, thereby reducing the chances of occupational injury.

BRIEF SUMMARY OF THE INVENTION

In view of, and in order to overcome, the various drawbacks of the conventional eyebrow tattoo machines during use, the inventor of the present invention conducted extensive research and experiment and finally succeeded in developing an eyebrow tattoo machine which operates with a swinging movement as well as an up-and-down movement and which therefore features enhanced operational efficiency.

It is an object of the present invention to provide an eyebrow tattoo machine capable of activating a swinging movement and an up-and-down movement so as to enable more effortless operation than the prior art would allow. The eyebrow tattoo machine includes a housing, a swinging movement-activating motor, an eccentric sleeve, and a tattoo needle actuation mechanism. The housing is provided therein with a receiving space. A first end of the housing is provided with an opening while a second end of the housing allows passage of a power cord. Two opposite outer lateral sides of the housing are each provided with a threaded hole in communication with the receiving space, wherein each threaded hole threadedly receives a screw. The swinging movement-activating motor is located in the receiving space and adjacent to the second end of the housing. Moreover, the swinging movement-activating motor is electrically connected to the power cord so as to receive electricity from the power cord. One end of the swinging movement-activating motor is provided with a transmission shaft which extends toward the first end of the housing and around which the eccentric sleeve is mounted. The end of the eccentric sleeve that faces away from the swinging movement-activating motor is protrudingly provided with an eccentric lever offset from the center of the eccentric sleeve. The tattoo needle actuation mechanism is located in the receiving space and adjacent to the first end of the housing. The tattoo needle actuation mechanism is provided with a tattoo needle at one end and a round-ended slot at the other end. An up-and-down movement-activating motor is provided in the tattoo needle actuation mechanism and is configured for driving the tattoo needle into up-and-down displacement along an axis of the eyebrow tattoo machine. The tattoo needle actuation mechanism is pressed against by the screws, and the eccentric lever extends into the round-ended slot so that, once the swinging movement-activating motor is turned on, the eccentric lever can drive the entire tattoo needle actuation mechanism to swing from side to side with respect to the axis of the eyebrow tattoo machine, using the screws as the fulcrum.

BRIEF DESCRIPTION OF THE SEVERAL VIEWS OF THE DRAWINGS

The structure as well as a preferred mode of use, further objects, and advantages of the present invention will be best understood by referring to the following detailed description of some illustrative embodiments in conjunction with the accompanying drawings, in which.

DETAILED DESCRIPTION OF THE INVENTION

The inventor has long been engaged in the research, development, and manufacture of eyebrow tattoo machines and like cosmetic products. In the process, the inventor has found that the transmission mechanism of the conventional eyebrow tattoo machines is designed only for activating up-and-down movement, which leaves much to be desired in terms of operation, and which demands a huge amount of physical and mental strength to be applied in order to complete the details of a tattoo design. In view of this, the inventor came up with the idea of providing a conventional eyebrow tattoo machine with an additional transmission mechanism so that an eyebrow tattooist can work on the details of a tattoo with ease. The provision of the additional transmission mechanism is intended to enable more effortless operation and reduce the chances of occupational injury.

Figure 1:
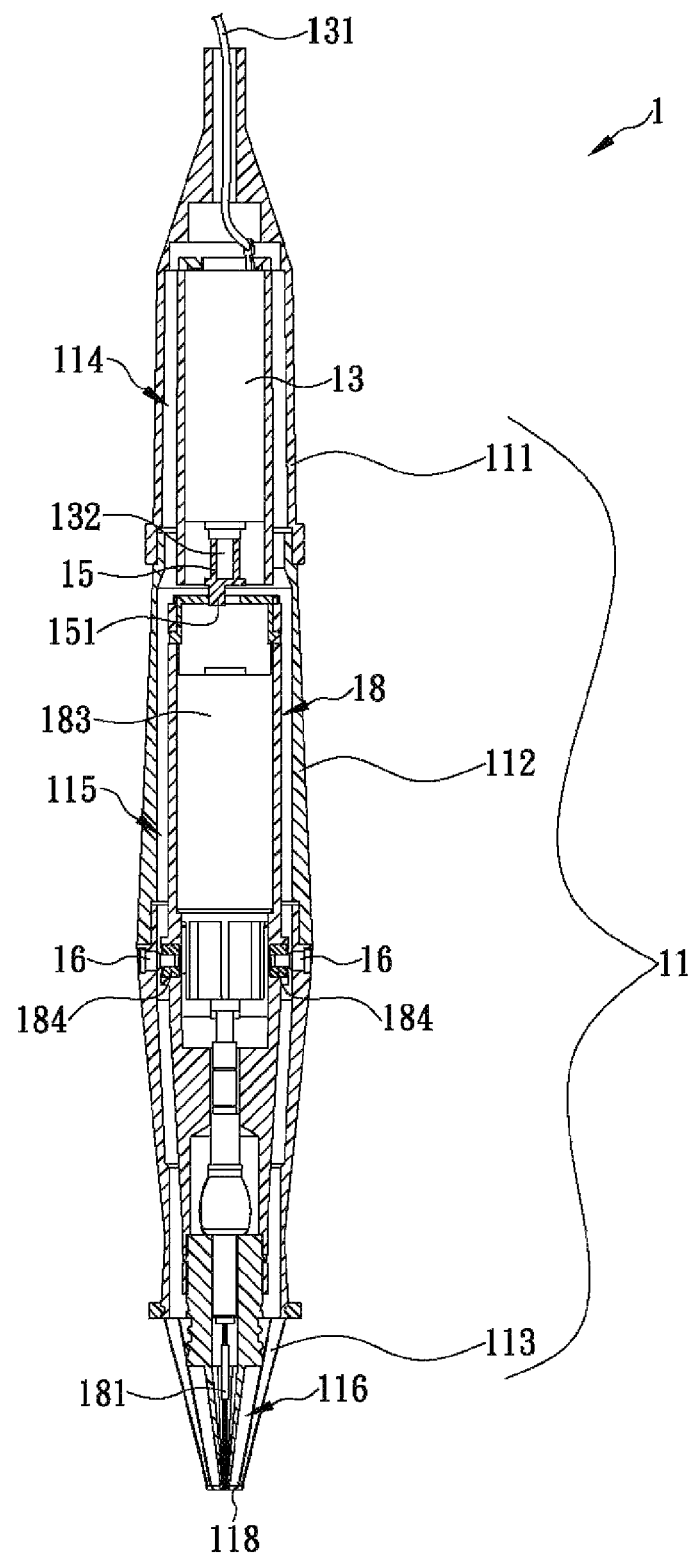
FIG. 1 is a sectional view of a preferred embodiment of the present invention.
Figure 2:
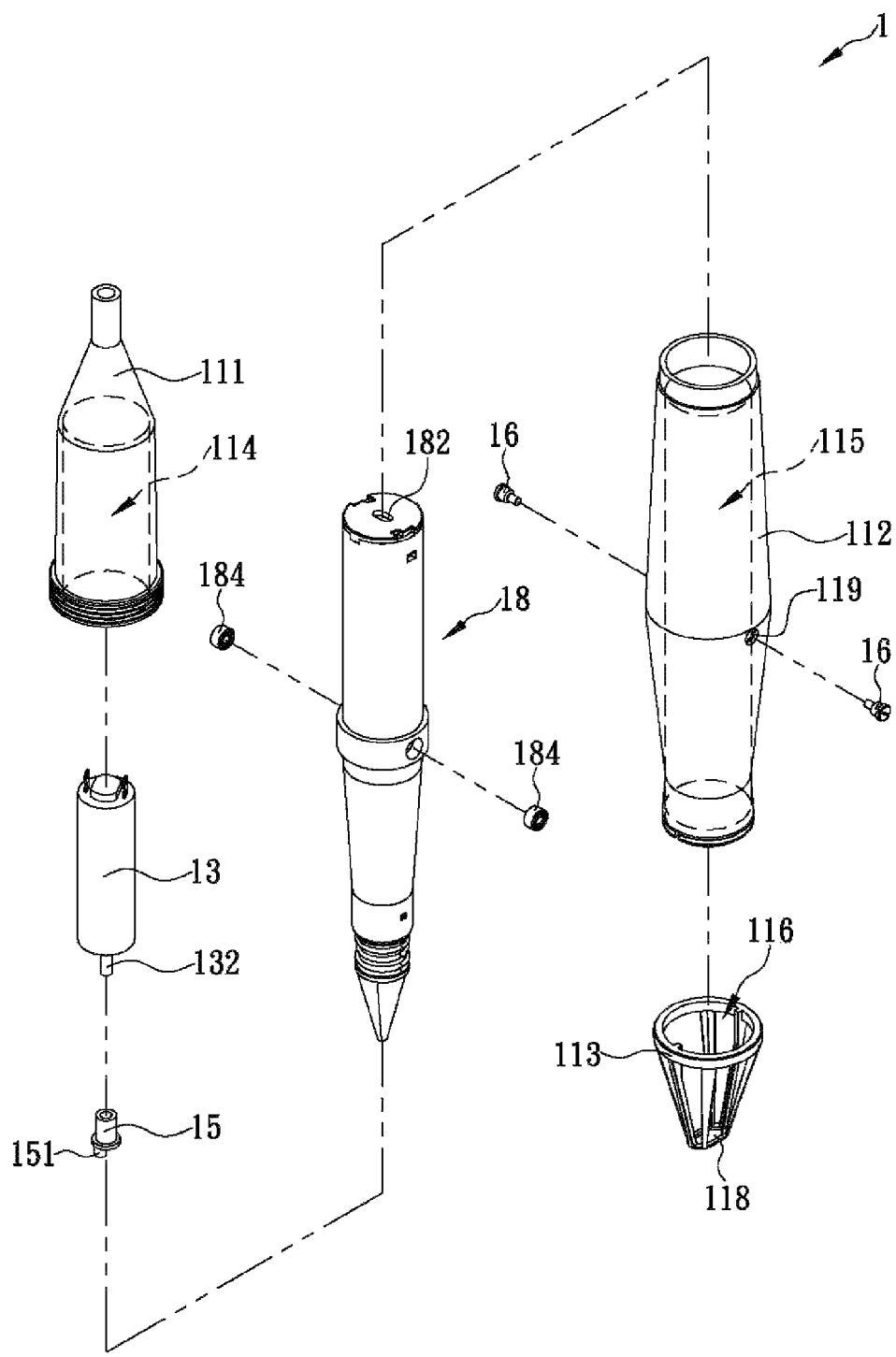
FIG. 2 is an exploded perspective view of the preferred embodiment of the present invention.

The present invention discloses an eyebrow tattoo machine capable of activating a swinging movement and an up-and-down movement. In a preferred embodiment of the present invention as shown in FIG. 1 and FIG. 2, the eyebrow tattoo machine 1 includes a housing 11, a swinging movement-activating motor 13, an eccentric sleeve 15, and a tattoo needle actuation mechanism 18. The housing 11 includes a first tube 111, a second tube 112, and a third tube 113 put together by, for example, threaded connection or mutual engagement. The first, second, and third tubes 111, 112, 113 are respectively provided therein with a first receiving space 114, a second receiving space 115, and a third receiving space 116. Once the first, second, and third tubes 111, 112, 113 are assembled together to form the housing 11, the first, second, and third receiving spaces 114, 115, 116 are in communication with one another. The housing 11 has a first end provided with an opening 118 and an opposite second end through which a power cord 131 extends. The swinging movement-activating motor 13 is provided in the first receiving space 114, enclosed by the first tube 111, and electrically connected to the power cord 131 in order to receive electricity therefrom. One end of the swinging movement-activating motor 13 is provided with a transmission shaft 132 which extends toward the first end of the housing 11. The second tube 112 has two opposite outer lateral sides each provided with a threaded hole 119. The threaded holes 119 are in communication with the second receiving space 115 and each have a screw 16 threadedly received therein.

As shown in FIG. 1 and FIG. 2, the eccentric sleeve 15 is mounted around the transmission shaft 132. The end of the eccentric sleeve 15 that faces away from the swinging movement-activating motor 13 is protrudingly provided with an eccentric lever 151 whose position is offset from the center of the eccentric sleeve 15. The tattoo needle actuation mechanism 18 is provided in the second receiving space 115 and enclosed by the second tube 112. A tattoo needle 181 is provided at one end of the tattoo needle actuation mechanism 18, located in the third receiving space 116, and enclosed by the third tube 113. The other end of the tattoo needle actuation mechanism 18 is provided with a round-ended slot 182. The eccentric lever 151 extends into the round-ended slot 182 so that the tattoo needle actuation mechanism 18 can be driven to swing from side to side by the swinging movement-activating motor 13, as explained in more detail below. The tattoo needle actuation mechanism 18 is provided therein with an up-and-down movement-activating motor 183 for driving the tattoo needle 181 into up-and-down displacement along an axis of the eyebrow tattoo machine 1. To prevent the tattoo needle 181 from swinging to an excessively large extent, the opening 118 at the first end of the housing 11 may be formed as a second round-ended slot. Thus, when driven by the swinging movement-activating motor 13 and the tattoo needle actuation mechanism 18, the tattoo needle 181 will swing from side to side and be displaced up and down within the range of the second round-ended slot. Also, the tattoo needle actuation mechanism 18 has two opposite outer lateral sides each provided with a bearing 184. The bearings 184 correspond in position to the threaded holes 119 and are pressed against by the screws 16 respectively. The tattoo needle 181 can therefore be swung from side to side with respect to the axis of the eyebrow tattoo machine 1, using the screws 16 as the fulcrum. In addition to serving as the fulcrum of the swinging movement of the tattoo needle actuation mechanism 18, the screws 16 prevent the tattoo needle actuation mechanism 18 from swinging excessively, which, if not prevented, will damage the transmission shaft 132 of the swinging movement-activating motor 13 and the eccentric sleeve 15. The bearings 184, on the other hand, make it possible for the tattoo needle actuation mechanism 18 to swing smoothly from side to side.

Figure 3:
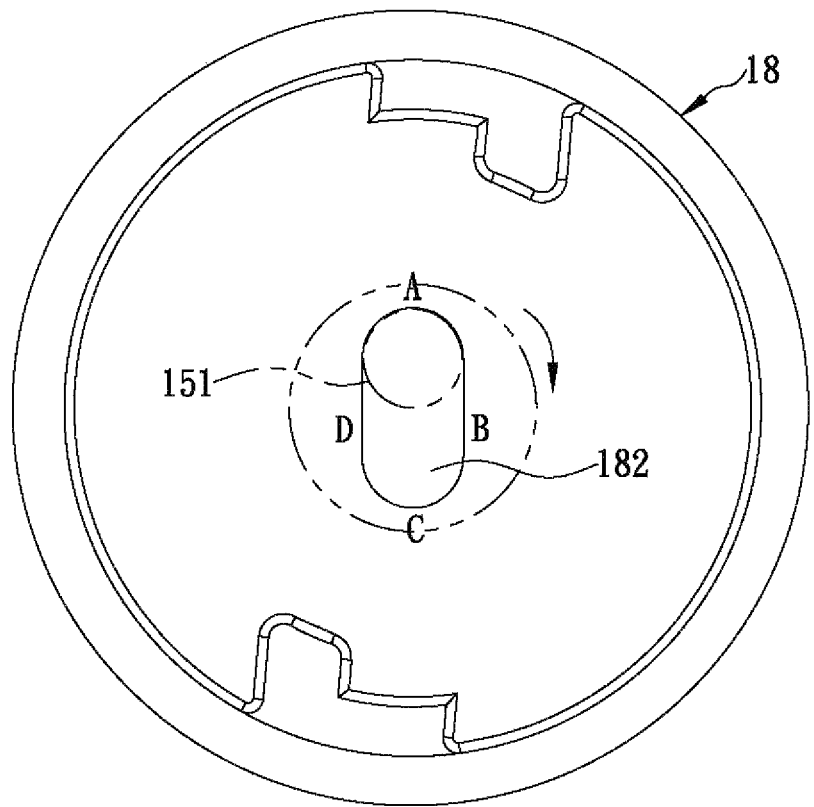
FIG. 3 is a schematic assembled view of the eccentric lever and the tattoo needle actuation mechanism of the present invention.
Figure 4:
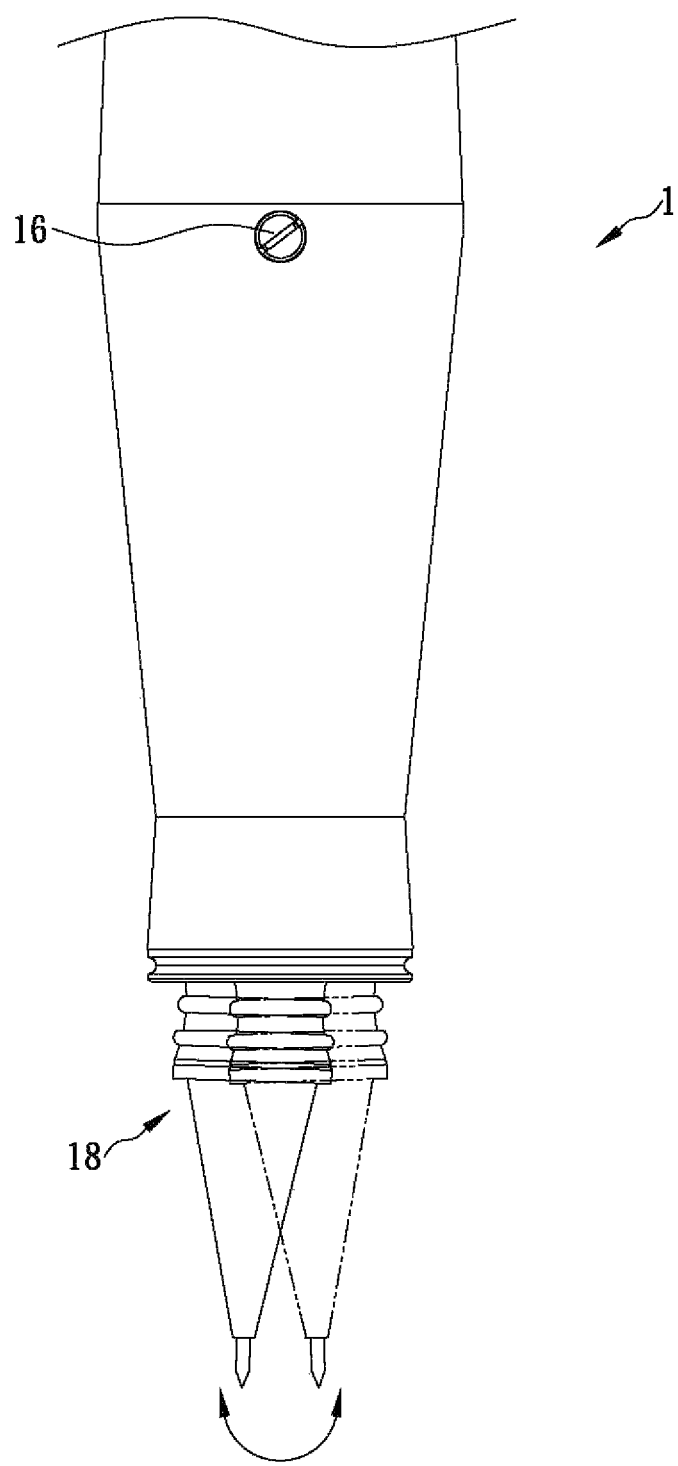
FIG. 4 schematically shows how the tattoo needle actuation mechanism of the present invention moves.

Referring to FIG. 3 and FIG. 4, the greatest diameter of the round-ended slot 182 is greater than the diameter of the eccentric lever 151 so that the eccentric lever 151 can slide in the round-ended slot 182. When the transmission shaft 132 drives the eccentric lever 151 to rotate (see FIG. 1), the eccentric lever 151 is moved, for example, from point A of the round-ended slot 182 sequentially to points B, C, D and then back to point A. As the eccentric lever 151 will glide from point A to point C and vice versa, the screws 16, which serve as the fulcrum, will not be forcefully pressed and are therefore kept from damage. More specifically, when the eccentric lever 151 is moved from point A toward point B, it is limited by, and thus applies a force to, the inner wall of the round-ended slot 182, causing the top end of the tattoo needle actuation mechanism 18 to displace toward the right side of FIG. 3. Now that the middle section of the tattoo needle actuation mechanism 18 is pressed against by the screws 16, the bottom end of the tattoo needle actuation mechanism 18 is displaced toward the left side of FIG. 4 as a result, allowing the eccentric lever 151 to slide to point C while being rotated. When subsequently moved from point C toward point D, the eccentric lever 151 is again limited by, and thus applies a force to, the inner wall of the round-ended slot 182, causing the top end of the tattoo needle actuation mechanism 18 to displace toward the left side of FIG. 3. With the screws 16 pressing against the middle section of the tattoo needle actuation mechanism 18, the bottom end of the tattoo needle actuation mechanism 18 is now displaced toward the right side of FIG. 4, allowing the eccentric lever 151 to slide to point A while being rotated. Thus, the tattoo needle actuation mechanism 18 is swung from side to side. The swinging movement not only increases the tattooing range of the eyebrow tattoo machine 1 when dealing with the details of a tattoo design, making the tattoo operation more efficient, but also helps create the visual effect that the resultant eyebrow tattoos have high hair density and great hair volume.

While the invention herein disclosed has been described by means of specific embodiments, numerous modifications and variations could be made thereto by those skilled in the art without departing from the scope of the invention set forth in the claims.

What is claimed is:

1. An eyebrow tattoo machine capable of activating a swinging movement and an up-and-down movement, comprising:

a housing provided therein with a receiving space, the housing having a first end provided with an opening and a second end through which a power cord passes;

a swinging movement-activating motor provided in the housing and adjacent to the second end of the housing, the swinging movement-activating motor being electrically connected to the power cord in order to receive electricity therefrom, the swinging movement-activating motor having an end provided with a transmission shaft, the transmission shaft extending toward the first end of the housing;

an eccentric sleeve mounted around the transmission shaft, the eccentric sleeve having an end which faces away from the swinging movement-activating motor and is protrudingly provided with an eccentric lever, the eccentric lever being offset from a center of the eccentric sleeve; and a tattoo needle actuation mechanism positioned in the housing in a way that allows the tattoo needle actuation mechanism to swing from side to side, the tattoo needle actuation mechanism being adjacent to the first end of the housing and having an end provided with a tattoo needle and an opposite end provided with a round-ended slot, the tattoo needle actuation mechanism being provided therein with an up-and-down movement-activating motor for driving the tattoo needle into up-and-down displacement along an axis of the eyebrow tattoo machine, the eccentric lever extending into the round-ended slot of the tattoo needle actuation mechanism in order to push an inner wall of the round-ended slot and thereby swing the entire tattoo needle actuation mechanism from side to side with respect to the axis of the eyebrow tattoo machine when the swinging movement-activating motor drives the eccentric lever to rotate.

2. The eyebrow tattoo machine of claim 1, wherein the housing has two opposite outer lateral sides each provided with a threaded hole in communication with the receiving space, and two screws are inserted in and fixed at the threaded holes respectively and press against a middle section of the tattoo needle actuation mechanism, thus enabling the entire tattoo needle actuation mechanism to swing from side to side with respect to the axis of the eyebrow tattoo machine, with the screws serving as a fulcrum.

3. The eyebrow tattoo machine of claim 2, wherein the tattoo needle actuation mechanism has two opposite outer lateral sides each provided with a bearing, the bearings corresponding in position to the threaded holes respectively, the screws pressing against the bearings respectively so that the tattoo needle can swing from side to side with respect to the axis of the eyebrow tattoo machine, with the screws serving as the fulcrum.

4. The eyebrow tattoo machine of claim 3, wherein the opening at the first end of the housing is formed as a second round-ended slot so that the tattoo needle, when driven by the swinging movement-activating motor and the tattoo needle actuation mechanism, can swing from side to side and be displaced up and down within a range of the second round-ended slot.

5. The eyebrow tattoo machine of claim 4, wherein the housing comprises a plurality of tubes sequentially connected together.

6. The eyebrow tattoo machine of claim 5, wherein the tubes comprise a first tube, a second tube, and a third tube, the first tube corresponding in position to and enclosing the swinging movement-activating motor, the second tube corresponding in position to and enclosing the tattoo needle actuation mechanism, the third tube corresponding in position to and enclosing the tattoo needle.

* * * * *